United States Patent
Epstein et al.

(10) Patent No.: US 9,827,212 B2
(45) Date of Patent: Nov. 28, 2017

(54) COMPOSITIONS AND METHODS FOR TREATING ASTHMA AND OTHER LUNG DISEASES

(75) Inventors: Jonathan A. Epstein, Radnor, PA (US); Reynold Panettieri, Bensalem, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 459 days.

(21) Appl. No.: 13/256,560

(22) PCT Filed: Mar. 18, 2010

(86) PCT No.: PCT/US2010/027833
§ 371 (c)(1),
(2), (4) Date: Dec. 27, 2011

(87) PCT Pub. No.: WO2010/108013
PCT Pub. Date: Sep. 23, 2010

(65) Prior Publication Data
US 2012/0094967 A1    Apr. 19, 2012

(51) Int. Cl.
| | | |
|---|---|---|
| *A61K 31/573* | (2006.01) | |
| *A61K 31/165* | (2006.01) | |
| *A61K 31/167* | (2006.01) | |
| *A61K 31/46* | (2006.01) | |
| *A61K 31/522* | (2006.01) | |
| *A61P 11/08* | (2006.01) | |
| *A61P 11/00* | (2006.01) | |
| *A61P 11/14* | (2006.01) | |
| *A61P 11/06* | (2006.01) | |
| *A61K 31/16* | (2006.01) | |
| *A61K 31/439* | (2006.01) | |
| *A61K 45/06* | (2006.01) | |

(52) U.S. Cl.
CPC ............ *A61K 31/16* (2013.01); *A61K 31/165* (2013.01); *A61K 31/167* (2013.01); *A61K 31/439* (2013.01); *A61K 31/522* (2013.01); *A61K 31/573* (2013.01); *A61K 45/06* (2013.01)

(58) Field of Classification Search
CPC .... A61K 31/16; A61K 31/165; A61K 31/167; A61K 31/439
See application file for complete search history.

(56) References Cited

U.S. PATENT DOCUMENTS

| 7,135,493 B2 | 11/2006 | Urano et al. | |
|---|---|---|---|
| 7,314,953 B2 * | 1/2008 | Wiech | A61K 31/16 560/312 |
| 2003/0134865 A1 * | 7/2003 | Adcock et al. | 514/263.34 |
| 2004/0157930 A1 * | 8/2004 | Mascagni | A61K 31/165 514/575 |
| 2006/0270730 A1 | 11/2006 | Katopodis | |
| 2007/0190022 A1 | 8/2007 | Bacopoulos et al. | |
| 2008/0194579 A1 | 8/2008 | Garcia-Echeverria et al. | |
| 2008/0242643 A1 | 10/2008 | Dufresne et al. | |

FOREIGN PATENT DOCUMENTS

| WO | WO/00/08048 | 2/2000 |
|---|---|---|
| WO | WO/2004/063169 | 7/2004 |
| WO | WO/2004/072047 | 8/2008 |
| WO | WO/2008/096111 | 8/2008 |

OTHER PUBLICATIONS

Choi et al. in Clinical and Experimental Allergy 35:89-96 (2005).*
Dixon et al. in Experimental Biology and Medicine 1965 118:756.*
Tashimoto et al. in Allergology International 56:241-247 (2007).*
Nimmagadda et al. in Ann. Allergy Asthma Immunol. 1996, 77(5):345-55; quiz 355-6.*
"What is Asthma" in www.nhlbi.nih.gov/health/health-topics/topics/asthma/ (retrieved from the internet on Mar. 10. 2014).*
"What is Asthma" In http://www.nhlbi.nih.gov/health/health-topics/topics/asthma/. (retrieved from the internet Oct. 5, 2015).*
Michel, O. in Journal of Endotoxin Research 9(5), 293-300 (2003).*
Adcock et al., "Epigenetics and airways disease", Respiratory Research 2006, 7:21.
Barnes et al., "Histone acetylation and deacetylation: importance in inflammatory lung diseases", Eur Respir J 2005; 25: 552-563.
Ito et al., "Decreased Histone Deacetylase Activity in Chronic Obstructive Pulmonary Disease", N. Engl. J. Med. 2005, 352;19 1967-1976.
Ito et al., "A molecular mechanism of action of theophylline:Induction of histone deacetylase activity to decrease inflammatory gene expression", Pnas 2002, vol. 99, No. 13, 8921-8926.
Ito et al., "Histone deacetylase 2—mediated deacetylation of the glucocorticoid receptor enables NF-κB suppression", Jour of Exp Medicine 2006, vol. 203, No. 1: 7-13.

* cited by examiner

*Primary Examiner* — Dennis Heyer
(74) *Attorney, Agent, or Firm* — Mark S. Cohen; Pearl Cohen Zedek Latzer Baratz LLP

(57) ABSTRACT

The present invention provides methods for dilating the bronchi or bronchioles and relaxing a pulmonary smooth muscle in a subject by treating the subject with a pharmaceutical composition, which includes a Histone deacetylase (HDAC) inhibitor. The ability to dilate the bronchi or bronchioles and relax a pulmonary smooth muscle according to the methods of the invention allows treating, alleviating, or inhibiting bronchoconstrictive diseases or disorders and symptoms associated or derived from bronchoconstrictive diseases.

12 Claims, 9 Drawing Sheets

HDAC Inhibitor (TSA)

```
        IP                      IP                    IN   IN   IN
        AF                      AF                    AF   AF   AF
    //------------------------//----------------------//-----//-----//
Day     0                       14                    25   26   27
                                                      TSA  TSA  TSA
                                                      IP   IP   IP
```

Conditions:
1.) Naïve
2.) AF only
3.) DMSO only (Vehicle control)
4.) DMSO + AF
5.) TSA/DMSO
6.) TSA/DMSO + AF
7.) DEX only
8.) DEX + AF
9.) DEX+ TSA+AF

COMPOSITIONS AND METHODS FOR TREATING ASTHMA AND OTHER LUNG DISEASES

CROSS-REFERENCE TO RELATED APPLICATIONS

This application is a National Phase Application of PCT International Application PCT/US10/27833, filed Mar. 18, 2010, which claims priority to U.S. Patent Application 61/161,305, filed Mar. 18, 2009, each of which is incorporated by reference herein in its entirety.

FIELD OF THE INVENTION

The invention related to compositions and methods for treating asthma and other lung diseases. Specifically, the invention relates to administering a Histone deacetylase (HDAC) inhibitor to treat asthma and other lung diseases.

BACKGROUND OF THE INVENTION

Asthma is a disease of variable airflow obstruction, bronchial hyperresponsiveness, and airway inflammation. Although most patients respond to conventional therapies, a substantial percentage of patients have severe or refractory asthma manifested by frequent exacerbations and irreversible airflow limitation and airway inflammation despite maximal medical therapy. Patients with severe asthma also disproportionately utilize healthcare resources, and have more adverse effects from high doses of medication. The search for new therapies for severe asthmatics continues.

SUMMARY OF THE INVENTION

In one embodiment, the invention provides a method for dilating the bronchi or bronchioles in a subject in need thereof, comprising the step of administering to a subject a composition comprising a histone deacetylase (HDAC) inhibitor, thereby dilating the bronchi or bronchioles in a subject.

In another embodiment, the invention provides a method of treating a subject afflicted with a bronchoconstrictive disorder, comprising the step of administering to a subject a composition comprising a histone deacetylase (HDAC) inhibitor, thereby treating a subject afflicted a bronchoconstrictive disorder.

In another embodiment, the invention provides a method of ameliorating the symptoms associated with a bronchoconstrictive disorder in a subject, comprising the step of administering to a subject a composition comprising a histone deacetylase (HDAC) inhibitor, thereby ameliorating the symptoms associated with a bronchoconstrictive disorder.

In another embodiment, the invention provides a method of preventing a bronchoconstrictive disorder or symptoms associated with a bronchoconstrictive disorder in a patient, comprising the step of administering to a subject a composition comprising a histone deacetylase (HDAC) inhibitor, thereby preventing a bronchoconstrictive disorder or symptoms associated with a bronchoconstrictive disorder.

In another embodiment, the invention provides a method of relaxing a pulmonary smooth muscle in a subject in need thereof, comprising the step of administering to a subject a composition comprising a histone deacetylase (HDAC) inhibitor, thereby relaxing a pulmonary smooth muscle in a subject in need thereof.

In another embodiment, the invention provides a method of reversing the effects of drug-induced broncho-constriction in a subject, comprising the step of administering to a subject a composition comprising a histone deacetylase (HDAC) inhibitor, thereby reversing the effects of drug-induced broncho-constriction in a subject.

In another embodiment, the invention provides a method for treating an asthma or a lung disease in a subject, the method comprising the step of administering to said subject a therapeutically effective amount of a histone deacetylase (HDAC) inhibitor, wherein said inhibitor is Trichostatin A (TSA), thereby treating said disease in said subject.

In another embodiment, the invention provides a pharmaceutical composition for treating an asthma or a lung disease in a subject, the composition comprising a histone deacetylase (HDAC) inhibitor, wherein said inhibitor is Trichostatin A (TSA), and wherein said inhibitor is present in an amount effective to treat said disease in said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figures 1A, 1B:
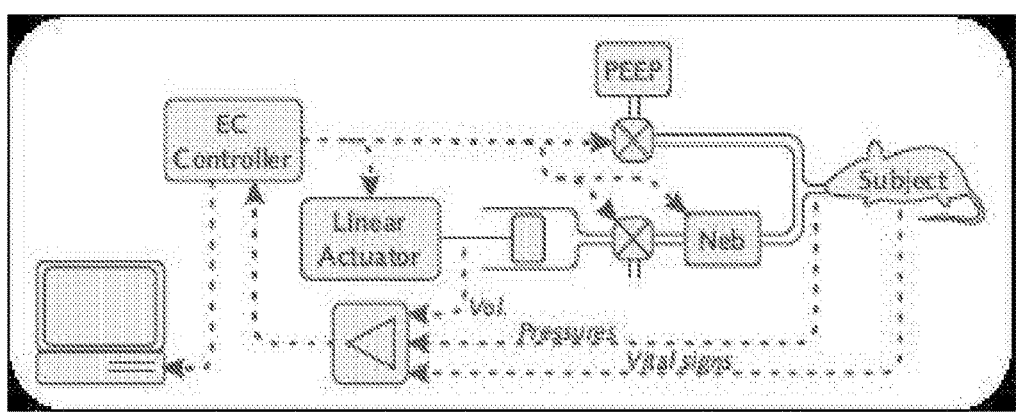
FIG. 1A. Experimental design with a timeline of experimental treatments. Animals were sensitized with two intraperitoneal (i.p.) injections at day 0 and day 14 with 20 µg of *Aspergillus Fumigatus* (AF) antigen. Three intranasal (i.n.) challenges of 25 µg of AF were performed, once a day for the three days before the animal was sacrificed. Additional animals were treated with the HDAC inhibitor, trichostatin (TSA), which was i.p. injected once a day for the three days before the animals were sacrificed. The animals were sacrificed on day 28 (or 1 day after the last challenge).
FIG. 1B. FlexiVent System Overview. FlexiVent is a modular, multi-functional device that performs both mechanical ventilation and detailed measurements of respiratory mechanics in subjects FIG. 2A. Western blot analysis of lysates from wild-type mouse lung, human airway smooth muscle cells, and lung epithelial cells using anti-Hdac1, anti-Hdac2, anti-Hdac3, anti-Hdac4, anti-Hdac5, anti-Hdac6, anti-Hdac8, and anti-Hdac10 antibodies was performed. Glyceraldehyde 3-phosphate dehydrogenase (GAPDH) is used as a loading control.

In one embodiment, provided herein is a method for dilating the bronchi, bronchioles, or both in a subject in need thereof, comprising the step of administering to a subject a composition comprising a histone deacetylase (HDAC) inhibitor, thereby dilating the bronchi, bronchioles, or both in a subject in need thereof.

In another embodiment, provided herein is a method for preventing the collapse of the bronchi, bronchioles, or both in a subject, comprising the step of administering to a subject a composition comprising a histone deacetylase (HDAC) inhibitor, thereby preventing the collapse of the bronchi, bronchioles, or both in a subject.

In another embodiment, provided herein is a method for reversing a collapse of the bronchi, bronchioles, or both in a subject, comprising the step of administering to a subject a composition comprising a histone deacetylase (HDAC) inhibitor, thereby reversing a collapse of the bronchi, bronchioles, or both in a subject.

In another embodiment, dilating comprises smooth muscle relaxation. In another embodiment, dilating comprises rapid smooth muscle relaxation. In another embodiment, dilating the bronchi and/or the bronchioles comprises decreasing airway resistance and thereby facilitating airflow. In another embodiment, dilating is short-term dilating. In another embodiment, dilating is long-term dilating. In another embodiment, short-term dilating provides quick relief from acute bronchoconstriction. In another embodiment, long-term dilating provides control and prevention of symptoms.

In another embodiment, a subject is a human subject. In another embodiment, a subject is a mammal. In another embodiment, a subject is a rodent. In another embodiment, a subject is a mouse. In another embodiment, a subject is a rat. In another embodiment, a subject is a pet. In another embodiment, a subject is a farm animal. In another embodiment, a subject is a child. In another embodiment, a subject is an infant. In another embodiment, a subject is a teenager. In another embodiment, a subject is an adult. In another embodiment, a subject is a senior subject.

In another embodiment, a patient is a subject afflicted with an airway disease. In another embodiment, a patient is a subject afflicted with an airway disease as described herein. In another embodiment, a patient is a subject afflicted with a COPD. In another embodiment, a patient is a subject afflicted with a disease, which induces bronchoconstriction. In another embodiment, a patient is a subject in need of dilating the bronchi or bronchioles. In another embodiment, the terms patient and subject are used interchangeably.

In another embodiment, a subject in need of a method as described herein is a subject having breathing difficulties. In another embodiment, a subject in need of a method as described herein is a subject afflicted with an obstructive lung disease. In another embodiment, a subject in need of a method as described herein is a subject afflicted with chronic obstructive pulmonary disease (COPD). In another embodiment, a subject in need of a method as described herein is a subject afflicted with bronchiolitis. In another embodiment, a subject in need of a method as described herein is a subject afflicted with a restrictive lung disease. In another embodiment, a subject in need of a method as described herein is a subject afflicted with a disorder of the respiratory muscles.

In another embodiment, a disorder of the respiratory muscles comprises anatomical sites ranging from the cerebral cortex to the alveolar sac. In another embodiment, a disorder of the respiratory muscles comprises weakness of the respiratory muscles. In another embodiment, a disorder of the respiratory muscles comprises primary neurologic and/or neuromuscular disorders. In another embodiment, a disorder of the respiratory muscles comprises structural abnormalities of the thoracic cage, such as scoliosis or flail chest. In another embodiment, a disorder of the respiratory muscles comprises hyperinflation.

In another embodiment, a histone deacetylase (HDAC) inhibitor is a pulmonary smooth muscle relaxant. In another embodiment, a HDAC inhibitor does not inhibit inflammation according to the methods and indications of the present invention. In another embodiment, a HDAC inhibitor is not an anti-inflammatory agent in the methods and indications as described herein. In another embodiment, a HDAC inhibitor has advantages over other bronchodilators, which work by binding to cell surface receptors that can be down regulated after prolonged use. In another embodiment, a HDAC inhibitor is a bronchodilator.

In one embodiment, the HDAC inhibitor is a hyroxamic acid. In another embodiment, the HDAC inhibitor is Trichostatin A (TSA). In another embodiment, the HDAC inhibitor is Vorinostat (rINN), which in another embodiment is suberoylanilide hydroxamic acid (SAHA). In another embodiment, the HDAC inhibitor is a cyclic tetrapeptide. In another embodiment, the HDAC inhibitor is a benzamide. In another embodiment, the HDAC inhibitor is an electrophilic ketone. In another embodiment, the HDAC inhibitor is an aliphatic acid group of compounds such as phenylbutyrate or valproic acid. In another embodiment, the HDAC inhibitor is Belinostat/PXD101. In another embodiment, the HDAC inhibitor is MS275. In another embodiment, the HDAC inhibitor is LAQ824/LBH589. In another embodiment, the HDAC inhibitor is CI994. In another embodiment, the HDAC inhibitor is MGCD0103.

In another embodiment, administering is injecting. In another embodiment, administering is topically administering. In another embodiment, administering is administering via inhalation. In another embodiment, administering is intranasal administration. In another embodiment, administering is enterally administering. In another embodiment, administering is orally administering. In another embodiment, administering is parenterally administering. In another embodiment, administering is intravenously administering. In another embodiment, administering is intramuscularly administering. In another embodiment, administering is intraperitonealy administering. In another embodiment, administering is intravenously administering.

In another embodiment, the composition is an oral pharmaceutical composition. In another embodiment, the composition is an inhaled dosage form. In another embodiment, the composition is an aerosol dosage form. In another embodiment, the composition is in an oral dosage form. In another embodiment, the composition is in a capsule. In another embodiment, the composition is in a powder. In another embodiment, the composition is in a solution. In another embodiment, the composition is in a suspension. In another embodiment, the composition is in a tablet. In another embodiment, the composition is in a buccal tablet. In another embodiment, the composition is in a sublingual tablet. In another embodiment, the composition is in an ampule. In another embodiment, the composition is in an emulsion. In another embodiment, the composition is in a spray. In another embodiment, the composition is in syrup.

In one embodiment, the subject is insensitive to steroid treatment. In another embodiment, the subject is resistant to steroid treatment. In another embodiment, the subject is not responsive to steroid treatment. In another embodiment, the bronchoconstriction is refractory to steroid treatment. In another embodiment, the bronchoconstriction is insensitive to steroid treatment. In another embodiment, the bronchoconstriction is resistant to steroid treatment. In another embodiment, the bronchoconstriction is not responsive to steroid treatment. In another embodiment, the disease or disorder to be treated using the methods of the present invention is refractory to steroid treatment. In another embodiment, the disease or disorder to be treated using the methods of the present invention is insensitive to steroid treatment. In another embodiment, the disease or disorder to be treated using the methods of the present invention is resistant to steroid treatment. In another embodiment, the disease or disorder to be treated using the methods of the present invention is non-responsive to steroid treatment.

In one embodiment, the composition further comprises a steroid. In another embodiment, the steroid is a synthetic member of the glucocorticoid class. In another embodiment, the steroid is dexamethasone. In another embodiment, the composition further comprises cortisone. In another embodiment, the composition further comprises betamethasone.

In another embodiment, the composition further comprises a beta2 agonist. In another embodiment, the composition further comprises salbutamol. In another embodiment, the composition further comprises levosalbutamol. In another embodiment, the composition further comprises terbutaline. In another embodiment, the composition further comprises pirbuterol. In another embodiment, the composition further comprises procaterol. In another embodiment, the composition further comprises metaproterenol. In another embodiment, the composition further comprises fenoterol. In another embodiment, the composition further comprises bitolterol mesylate. In another embodiment, the composition further comprises salmeterol. In another embodiment, the composition further comprises formoterol. In another embodiment, the composition further comprises bambuterol. In another embodiment, the composition further comprises clenbuterol. In another embodiment, the composition further comprises indacaterol.

In another embodiment, the composition further comprises ipatropium bromide. In another embodiment, the composition further comprises theophylline. In another embodiment, the composition comprises any combination of the active pharmaceutical ingredients described herein.

In another embodiment, administering a composition comprising HDAC inhibitor is administering between 0.1 mg/kg to 5 mg/kg HDAC inhibitor. In another embodiment, administering a composition comprising HDAC inhibitor is administering between 0.1 mg/kg to 0.5 mg/kg HDAC inhibitor. In another embodiment, administering a composition comprising HDAC inhibitor is administering between 0.5 mg/kg to 1 mg/kg HDAC inhibitor. In another embodiment, administering a composition comprising HDAC inhibitor is administering between 0.5 mg/kg to 1.5 mg/kg HDAC inhibitor. In another embodiment, administering a composition comprising HDAC inhibitor is administering between 1 mg/kg to 3 mg/kg HDAC inhibitor. In another embodiment, administering a composition comprising HDAC inhibitor is administering between 2 mg/kg to 4 mg/kg HDAC inhibitor. In another embodiment, administering a composition comprising HDAC inhibitor is administering between 3 mg/kg to 5 mg/kg HDAC inhibitor.

In another embodiment, a daily dose of a HDAC inhibitor ranges between 0.1 mg/kg to 5 mg/kg HDAC inhibitor. In another embodiment, a daily dose of a HDAC inhibitor ranges between 0.1 mg/kg to 0.5 mg/kg HDAC inhibitor. In another embodiment, a daily dose of a HDAC inhibitor ranges between 0.5 mg/kg to 1 mg/kg HDAC inhibitor. In another embodiment, a daily dose of a HDAC inhibitor ranges between 0.5 mg/kg to 1.5 mg/kg HDAC inhibitor. In another embodiment, a daily dose of a HDAC inhibitor ranges between 1 mg/kg to 3 mg/kg HDAC inhibitor. In another embodiment, a daily dose of a HDAC inhibitor ranges between 2 mg/kg to 4 mg/kg HDAC inhibitor. In another embodiment, a daily dose of a HDAC inhibitor ranges between 3 mg/kg to 5 mg/kg HDAC inhibitor.

In another embodiment, provided herein a method of treating a subject afflicted with a bronchoconstrictive disorder, comprising the step of administering to a subject a composition comprising a histone deacetylase (HDAC) inhibitor, thereby treating a subject afflicted a bronchoconstrictive disorder. In another embodiment, the bronchoconstrictive disorder is not asthma. In another embodiment, COPD is not asthma. In another embodiment, the HDAC inhibitor comprises a bronchodilating effect. In another embodiment, the HDAC inhibitor is a bronchodilator. In another embodiment, the HDAC inhibitor is a bronchodilator and not an anti-inflammatory agent.

In another embodiment, provided herein a method of treating bronchoconstriction in a patient afflicted with asthma. In another embodiment, a HDAC inhibitor reverses bronchoconstriction in a patient afflicted with asthma. In another embodiment, a HDAC inhibitor alleviates bronchoconstriction in a patient afflicted with asthma. In another embodiment, a HDAC inhibitor inhibits bronchoconstriction in a patient afflicted with asthma.

In another embodiment, provided herein a method of dilating the bronchi and bronchioles in a patient afflicted with asthma. In another embodiment, a HDAC inhibitor reverses bronchoconstriction in a patient afflicted with asthma by dilating the bronchi and bronchioles. In another embodiment, a HDAC inhibitor alleviates bronchoconstriction in a patient afflicted with asthma by dilating the bronchi and bronchioles. In another embodiment, a HDAC inhibitor inhibits bronchoconstriction in a patient afflicted with asthma by dilating the bronchi and bronchioles.

In another embodiment, a HDAC inhibitor reverses bronchoconstriction in a patient afflicted with a COPD. In another embodiment, a HDAC inhibitor alleviates bronchoconstriction in a patient afflicted with a COPD. In another embodiment, a HDAC inhibitor inhibits bronchoconstriction in a patient afflicted with a COPD.

In another embodiment, a HDAC inhibitor reverses bronchoconstriction in a patient afflicted with a COPD by dilating the bronchi and bronchioles. In another embodiment, a HDAC inhibitor alleviates bronchoconstriction in a patient afflicted with a COPD by dilating the bronchi and bronchioles. In another embodiment, a HDAC inhibitor inhibits bronchoconstriction in a patient afflicted with a COPD by dilating the bronchi and bronchioles.

In another embodiment, the HDAC inhibitor does not reduce inflammation associated with the bronchoconstrictive disorder. In another embodiment, the HDAC inhibitor acts as a bronchodilator and not as an anti-inflammatory agent. In another embodiment, the HDAC inhibitor does not affect lung inflammation. In another embodiment, the HDAC inhibitor does not reduce lung inflammation. In another embodiment, the HDAC inhibitor does not induce cytokines associated with inflammation. In another embodiment, the HDAC inhibitor does not induce cytokines associated with lung inflammation.

In another embodiment, the bronchoconstrictive disorder is Chronic Obstructive Pulmonary Disease (COPD). In another embodiment, COPD is Chronic Airflow Limitation (CAL). In another embodiment, COPD is emphysema. In another embodiment, provided herein a method of treating a subject suffering from symptoms associated with emphysema. In another embodiment, provided herein a method of reducing symptoms associated with emphysema. In another embodiment, provided herein a method of inhibiting symptoms associated with emphysema. In another embodiment, symptoms associated with emphysema include shortness of breath on exertion and later at rest, hyperventilation, pursed-lipped breathing, central cyanosis, audible expiratory wheeze, asterixis, pitting peripheral edema, finger clubbing, and an expanded chest. In another embodiment, emphysema is mild emphysema.

In another embodiment, allergic rhinitis is a COPD. In another embodiment, COPD is a disease of the lungs in which the airways become narrowed. In another embodiment, allergic rhinitis is a COPD. In another embodiment, COPD is a disease characterized by limitation of the flow of air to and from the lungs causing shortness of breath. In another embodiment, asthma is not a COPD. In another embodiment, in contrast to asthma, in COPD the limitation of airflow is poorly reversible and usually gradually gets worse over time.

In one embodiment, obstructive respiratory disease is a disease of luminal passages in the lungs, marked by dyspnea, tachypnea, or auscultatory or radiological signs of airway obstruction. Obstructive respiratory disease comprises asthma, acute pulmonary infections, acute respiratory distress syndrome, chronic obstructive pulmonary disease, rhinitis, and allergic rhinitis. In one embodiment, the pathophysiology is attributed to obstruction of air flow due to constriction of airway lumen smooth muscle and accumulation of infiltrates in and around the airway lumen.

In one embodiment, asthma is a disease process wherein the bronchi may be narrowed, making breathing difficult. In one embodiment, symptoms comprise wheezing, difficulty breathing (particularly exhaling air), tightness in the chest, or a combination thereof. In one embodiment, factors which can exacerbate asthma include rapid changes in temperature or humidity, allergies, upper respiratory infections, exercise, stress, smoke (cigarette), or a combination thereof.

In one embodiment, rhinitis comprises an inflammation of the mucous membrane of the nose. In one embodiment, allergic rhinitis is an inflammatory response in the nasal passages to an allergic stimulus. In one embodiment, symptoms comprise nasal congestion, sneezing, runny, itchy nose, or a combination thereof.

In one embodiment, chronic obstructive pulmonary disease is a progressive disease process that most commonly results from smoking. In one embodiment, chronic obstructive pulmonary disease comprises difficulty breathing, wheezing, coughing, which may be a chronic cough, or a combination thereof. In one embodiment, chronic obstructive pulmonary disease may lead to health complications, which in one embodiment, may comprise bronchitis, pneumonia, lung cancer, or a combination thereof.

In another embodiment, provided herein is a method of treating airflow obstruction comprising administering to a subject in need a HDAC inhibitor. In another embodiment, provided herein a method of treating breathlessness comprising administering to a subject in need a HDAC inhibitor. In another embodiment, provided herein a method of alleviating symptoms associated with bronchial adenoma. In another embodiment, symptoms associated with bronchial adenoma include: dyspnea, stridor, wheezing, cough, or any combination thereof. In another embodiment, provided herein is a method of treating airflow obstruction due to bronchitis, pneumonia, lung cancer, or a combination thereof comprising administering to a subject in need a HDAC inhibitor. In another embodiment, provided herein is a method of treating airflow obstruction due to respiratory system cancer, which in one embodiment is Lung cancer, Oral cancer, Mouth cancer, Tongue cancer, Pharynx cancer, Larynx cancer, Throat cancer, Bronchial cancer, Small cell lung cancer, adult, Hypopharyngeal cancer, Oropharyngeal cancer, adult, Adenocarcinoma, Bronchiolo-Alveolar, comprising administering to a subject in need a HDAC inhibitor.

In another embodiment, provided herein a method of treating a COPD comprising administering to a subject in need a HDAC inhibitor and an anti-inflammatory agent. In another embodiment, provided herein a method of treating a COPD comprising administering to a subject in need a HDAC inhibitor which acts as a bronchodilator and an anti-inflammatory agent.

In another embodiment, COPD is bronchitis. In another embodiment, provided herein a method of reducing symptoms associated with bronchitis. In another embodiment, provided herein a method of reducing symptoms associated with bronchitis without reducing an inflammation associated with bronchitis. In another embodiment, provided herein a method of treating bronchitis comprising administering to a subject in need a HDAC inhibitor and an anti-inflammatory agent. In another embodiment, provided herein a method of treating bronchitis comprising administering to a subject in need a HDAC inhibitor, which acts as a bronchodilator and an anti-inflammatory agent.

In another embodiment, a HDAC inhibitor alleviates coughing associated with bronchitis. In another embodiment, a HDAC inhibitor alleviates symptoms associated with bronchiolitis. In another embodiment, a HDAC inhibitor alleviates symptoms associated with bronchiolitis in infants.

In another embodiment, a HDAC inhibitor alleviates coughing derived from bronchitis. In another embodiment, a HDAC inhibitor alleviates symptoms derived from bronchiolitis. In another embodiment, a HDAC inhibitor alleviates symptoms derived from bronchiolitis in infants.

In another embodiment, COPD is Chronic Airflow Obstruction (CAO). In another embodiment, COPD is bronchial hyper-responsiveness. In another embodiment, COPD is Chronic Airflow Obstruction comprises decreases in volumes and flow rates of gas during expiration. In another embodiment, Chronic Airflow Obstruction comprises forced expiratory volume in one second (FEV1) ranging from 350-910 ml. In another embodiment, a HDAC inhibitor increases FEV1.

In another embodiment, provided herein a method of ameliorating the symptoms associated with a bronchoconstrictive disorder in a subject, comprising the step of administering to a subject a composition comprising a histone deacetylase (HDAC) inhibitor, thereby ameliorating the symptoms associated with a bronchoconstrictive disorder.

In another embodiment, provided herein a method for the treatment, prevention, or amelioration of one or more symptoms of bronchoconstrictive disorders in a patient, comprising the step of administering to a patient a composition comprising a histone deacetylase (HDAC) inhibitor. In another embodiment, the bronchoconstrictive disorder is COPD.

In another embodiment, a bronchoconstrictive disorder is asthma, pediatric asthma, bronchial asthma, allergic asthma, or intrinsic asthma. In another embodiment, a bronchoconstrictive disorder is chronic bronchitis. In another embodiment, a bronchoconstrictive disorder is emphysema. In another embodiment, a bronchoconstrictive disorder is treated, prevented, or whose one or more symptoms are to be ameliorated is associated with COPD.

In another embodiment, provided herein a method of preventing a bronchoconstrictive disorder or symptoms associated with a bronchoconstrictive disorder in a patient, comprising the step of administering to a subject a composition comprising a histone deacetylase (HDAC) inhibitor.

In one embodiment, the methods described herein may be used to prevent a disease or disorder described herein by identifying a prone population, such as, inter alia, those with a family history of said disease or disorder, and applying the methods prophylactically.

In another embodiment, provided herein a method of relaxing a pulmonary smooth muscle in a subject in need thereof, comprising the step of administering to a subject a composition comprising a histone deacetylase (HDAC) inhibitor, thereby relaxing a pulmonary smooth muscle in a subject in need thereof.

In another embodiment, provided herein a method of preventing exaggeration of smooth muscle shortening. In another embodiment, provided herein a method of preventing exaggeration of pulmonary smooth muscle shortening. In another embodiment, provided herein a method of reversing exaggeration of pulmonary smooth muscle shortening.

In another embodiment, provided herein a method of inhibiting pulmonary smooth muscle shortening.

In another embodiment, provided herein a method of ameliorating symptoms associated with airway wall remodeling resulting from chronic inflammation. In another embodiment, provided herein a method of ameliorating symptoms associated with airway hyperresponsiveness. In another embodiment, provided herein a method of preventing excess accumulation of muscle mass and the mechanical augmentation of luminal narrowing promoted by airway submucosal thickening. In another embodiment, provided herein a method of reversing excess accumulation of muscle mass and the mechanical augmentation of luminal narrowing promoted by airway submucosal thickening. In another embodiment, provided herein a method of minimizing excess accumulation of muscle mass and the mechanical augmentation of luminal narrowing promoted by airway submucosal thickening.

In another embodiment, provided herein a method of reducing an abnormal sensitivity of airway muscle to contractile stimulation, as assessed during static, isometric force measurements. In another embodiment, provided herein a method of inhibiting an abnormal sensitivity of airway muscle to contractile stimulation, as assessed during static, isometric force measurements. In another embodiment, provided herein a method of correcting dysregulated airway smooth muscle contraction dynamics. In another embodiment, provided herein a method of reversing dysregulated airway smooth muscle contraction dynamics. In another embodiment, provided herein a method of regulating a dysregulated airway smooth muscle contraction dynamics. In another embodiment, provided herein a method of regulating pulmonary smooth-muscle proliferation. In another embodiment, provided herein a method of inhibiting pulmonary smooth-muscle proliferation.

In another embodiment, provided herein a method of reversing the effects of drug-induced broncho-constriction in a subject, comprising the step of administering to a subject a composition comprising a histone deacetylase (HDAC) inhibitor, thereby reversing the effects of drug-induced broncho-constriction in a subject. In another embodiment, reversing the effects of drug-induced broncho-constriction comprises relaxing a pulmonary smooth muscle. In another embodiment, relaxing a pulmonary smooth muscle is dilating the bronchi, bronchioles, or both.

In another embodiment, the drug is an inducer of a pulmonary smooth muscle alpha-receptor. In another embodiment, the drug is a selective inducer of a pulmonary smooth muscle alpha-receptor. In another embodiment, the drug stimulates histamine release. In another embodiment, the drug is an acetaldehyde. In another embodiment, the drug is a Beta-blocker. In another embodiment, the drug is penicillin. In another embodiment, the drug is aspirin. In another embodiment, the drug is an opiate.

In another embodiment, provided herein a method of reversing the effects of allergy-induced broncho-constriction in a subject, comprising the step of administering to a subject a composition comprising a histone deacetylase (HDAC) inhibitor, thereby reversing the effects of allergy-induced broncho-constriction in a subject.

In another embodiment, provided herein a method of inhibiting the effects of allergy-induced broncho-constriction in a subject, comprising the step of administering to a subject a composition comprising a histone deacetylase (HDAC) inhibitor, thereby inhibiting the effects of allergy-induced broncho-constriction in a subject.

In another embodiment, provided herein a method of reversing the effects of exercise-induced broncho-constriction in a subject, comprising the step of administering to a subject a composition comprising a histone deacetylase (HDAC) inhibitor, thereby reversing the effects of exercise-induced broncho-constriction in a subject.

In another embodiment, provided herein a method of inhibiting the effects of exercise-induced broncho-constriction in a subject, comprising the step of administering to a subject a composition comprising a histone deacetylase (HDAC) inhibitor, thereby inhibiting the effects of exercise-induced broncho-constriction in a subject.

In another embodiment, provided herein a method of utilizing a HDAC inhibitor for treating COPD, whereby the HDAC inhibitor comprises a vasodilator activity. In another embodiment, the fact that a HDAC inhibitor comprises a vasodilator activity is surprising. In another embodiment, the fact that a HDAC inhibitor comprises a vasodilator activity and not an anti-inflammatory activity is surprising. In another embodiment, the fact that a HDAC inhibitor comprises a vasodilator activity and not an anti-inflammatory activity in COPD settings is surprising. In another embodiment, HDAC inhibitors are beneficial as bronchodilators and do not support a role as significant anti-inflammatory agents in COPD.

Pharmaceutical Compositions and Methods of Administration

The HDAC inhibitors of the present invention and pharmaceutical compositions comprising same can be, in another embodiment, administered to a subject by any method known to a person skilled in the art, such as parenterally, paracancerally, transmucosally, transdermally, intramuscularly, intravenously, intra-dermally, subcutaneously, intraperitonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound (e.g. the mimetic compound, peptide or nucleotide molecule) and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compounds solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment of the present invention.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. These agents include, but are not limited to, chemotherapeutic agents. In another embodiment, these agents are appropriate for the disease or disorder that is being treated, as is well known in the art.

In one embodiment, the methods of the present invention comprise administering an active compound as the sole active ingredient. However, also encompassed within the scope of the present invention are methods for treating diseases and disorders that comprise administering the active compound in combination with one or more therapeutic agents.

In one embodiment, "treating" refers to either therapeutic treatment or prophylactic or preventative measures, wherein the object is to prevent or lessen the targeted pathologic condition or disorder as described hereinabove, while in another embodiment, "treating" may refer only to therapeutic treatment. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, prolonging patient survival, or a combination thereof.

It is to be understood that the composition for use in the methods of the present invention may comprise one or more HDAC inhibitor, consist of one or more HDAC inhibitors, or consist essentially of one or more HDAC inhibitors. Similarly, the claimed methods may comprise, consist essentially of or consist of the described steps. In some embodiments, the term "comprise" or "comprising" refers to the inclusion of the indicated active agent, such as a HDAC inhibitor or step, such as administering the HDAC inhibitor, as well as inclusion of other active agents, and pharmaceutically acceptable carriers, excipients, emollients, stabilizers, etc., as are known in the art. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components that facilitate the release of the active ingredient. In some embodiments, the term "consisting" refers to a composition, which contains the active ingredient and a pharmaceutically acceptable carrier or excipient.

EXAMPLES

Materials and Methods

Mice

Female mice were used. All animal protocols were approved by the animal use and care committee at the University of Pennsylvania.

Allergen Sensitization and Challenge

Mice were sensitized by intraperitoneal (I.P.) injections of 20 µg allergen, a protein extract of the ubiquitous, airborn fungus, *Aspergillus fumigatus* (AF), (Bayer Pharmaceuticals), in 100 µl PBS solution containing 2 mg of alum (Imject Alum, Pierce) on days 0 and 14 and challenged on days 25, 26, and 27 with 30 µl of Af extract in PBS (25 µg) intranasally (i.n.) (FIG. 1).

Trichostatin (TSA) Dosing

Mice received three intraperitoneal (I.P.) injections of 0.6 mg/kg of TSA (Sigma Aldrich) twice a day on days 25, 26, and 27 (FIG. 1).

Invasive Lung Function Measurements of Anesthetized, Cannulated Mice

Lung resistance, compliance, elastance, tissue damping, tissue elastance, and airway resistance were recorded using the FlexiVent system (SCIREQ Scientific Respiratory Equipment Inc). The FlexiVent System Overview is shown in FIG. 1B: FlexiVent is a modular, multi-functional device that performs both mechanical ventilation and detailed measurements of respiratory mechanics in subjects.

The mice were anesthetized by an I.P. injection of a Ketamine (100 mg/kg) and Xylazine (20 mg/kg) mixture. After anesthesia, a half centimeter incision was made from the rostal to caudal direction; the flap of skin was retracted and the connective tissue was dissected away, and the trachea was exposed. The trachea was then cannulated between the second and third cartilage rings with a blunt-end stub adapter. The cannula was secured with suture. The mice were next connected to the Flexivent system. All spontaneous respirations were stopped with an intramuscular injection of Pancuronium Bromide (3 mg/kg) and the mice were then mechanically ventilated at respiratory rate of 140 beats/per minute with 0.25 ml of tidal volume. The Flexivent system then briefly interrupted the mechanical ventilation to apply a test signal, or perturbation to measure the respiratory mechanics. The respiratory mechanics were then calculated from the data collected while the perturbation was applied. The animal's airway responsiveness was measured after the inhalation of nebulized saline and a series of nebulized treatments of increasing concentrations of methacholine (1.25, 5, 10, and 20 mg/ml). At the end of testing the mice were disconnected and processed for multiple organ, blood, and fluid removal. The mice were first exsanguinated through the optical artery. Then bronchoalveolar lavage was performed through the tracheal canula. Finally, the peritoneal and the thoracic cavity were opened, and the lungs were removed for protein and histological processing.

BAL Cell Count and Differential

After functional measurements were completed, lungs were lavaged with 1-ml aliquots of sterile saline through the tracheal cannula. After centrifuging (500 g for 10 min at 4° C.) the cell pellet was resuspended in RPMI. Differential cell counts were made from cytospin preparations as described (Elwood et al. 1991). Cells were identified as macrophages, eosinophils, neutrophils, and lymphocytes by standard morphology and at least 300 cells were counted under ×400 magnification. The percentage and absolute numbers of each cell type were then calculated. The supernatants were harvested and stored at −20° C. for further analysis.

IL-4, IL-6, and RANTES Determination

The levels of cytokine secreted into the supernatants of PCLS and bronchoalveolar lavage (BAL) fluid samples were determined by ELISA according to standard protocols as previously described (Banerjee et al. 2008). The cytokine amounts were calculated from the standard curves in each plate. The limits of detection were 5 pg/ml for IL-4 and IL-6 and RANTES standards. Recombinant mouse IL-4 and IL-6 and human RANTES were used as controls.

SDS-Polyacrylamide Gel Electrophoresis and Western Blot Analysis

Tissue lysates were prepared in lysis buffer consisting of 20 mmol/L Tris HCl (pH 7.5), 150 mmol/L NaCl, 1 mmol/L Na2EDTA, 1 mmol/L EGTA, 1% Triton X-100, 1 µg/mL leupeptin, 2.5 mmol/L sodium pyrophosphate, 1 mmol/L Na3VO4, 1 mmol/L β-glycerophosphate. 1 mmol/L phenylmethylsulfonyl fluoride was added before use. Total 100 microgram of samples were separated by 4-12% SDS-PAGE (Invitrogen) and transferred to PVDF membranes. We used antibodies to Hdac1 (1:1000, Cell Signaling), Hdac2 (1:1000, Invitrogen), Hdac3 (1:1000 dilution, Sigma), Hdac4 (1:1000, Cell Signaling), Hdac5 (1:1000, Cell Signaling), Hdac6 (1:1000, SantaCruz), Hdac8 (1:1000, SantaCruz), Hdac10 (1:1000, Sigma), and anti-GAPDH (1:5000, Sigma). Primary antibody binding was visualized by using the Westernbreeze Kit (Invitrogen) as described earlier and according to the manufacturer's instructions (ref Trivedi C M Nat Med and JBC).

HDAC Activity Assay

HDAC activity was measured as described previously (Trivedi et al. 2007). In brief, total extract was prepared from lung sections harvested from naïve mice, *Aspergillus* sensitized and challenged mice, naïve mice treated with TSA, *Aspergillus* sensitized and challenged mice treated with dexamethasone, *Aspergillus* sensitized and challenged mice treated with TSA and *Aspergillus* sensitized and challenged mice treated with a combination of dexamethasone and TSA. 50 µg of total extract was incubated with HDAC assay substrate and incubated at 30° C. for 60 min. After the addition of diluted activator reagent, samples were incubated at room temperature for 15 min, and readings were taken by fluorescent microplate reader at an excitation of 360 nm and emission of 450 nm. A standard curve was performed according to the manufacturer's protocol.

PCLS Preparation

Human lung slice preparation. Human PCLS were prepared as previously described (Cooper et al. 2008). Briefly, healthy whole human lungs were received from the NDRI, and the smallest lobe was dissected out and its main bronchus identified. The lobe was inflated using a 2% (wt/vol) low melting point agarose solution. Once the agarose had set, the lobe was sectioned, and cores of 8-mm diameter were made. The cores that contained a small airway by visual inspection were sliced at a thickness of 250 µm (Krumdieck Tissue Slicer; model no. MD4000; Alabama Research and Development) and collected in wells containing supplemented Ham's F-12 medium. Suitable airways (≤1-mm diameter) on slices were selected on the basis of the following criteria: presence of a full smooth muscle wall (i.e., cut perpendicular to direction of airway); presence of beating cilia to eliminate blood vessels; and unshared muscle walls at airway branch points to eliminate possible counteracting contractile forces. Each slice was approximated to contain ~98% parenchyma tissue; hence, all airways situated on a slice had sufficient parenchymal tissue to satisfy its own baseline tone. Adjacent slices containing contiguous segments of the same airway were paired to act as control to the variable tested and incubated at 37° C. on a rotating platform in a humidified air-CO2 (95-5%) incubator. Sections were placed in fresh media every 2-3 h during the remainder of day 1 and all of day 2 to rid the slice and media of agarose and endogenous substances released that could variably confound the production of inflammatory mediators and/or alter airway tone.

Three airways from each donor were used per condition; n values indicate the number of donors. Data are expressed as means± SEM. Statistical difference was shown by using a nonpaired t test.

Human ASM Cell Cultures.

Human ASM cells, plated on plastic without substrate, were derived from trachea obtained from the National Disease Research Interchange (NDRI; Philadelphia, Pa.). Human ASM cell culture was performed as described previously (Panettieri et al. 1989). Briefly, a segment of trachea just proximal to the carina was removed under sterile conditions, and the tracheal muscle was isolated, centrifuged and resuspended in buffer containing 0.2 mM CaCl2, 640 U/ml collagenase, 1.0 mg/ml soybean trypsin inhibitor, and 10 U/ml elastase. The tissue was enzymatically dissociated, filtered, and washed. Aliquots of the cell suspension were plated at a density of 1.0×104 cells/cm2. The cells were cultured in Ham's F-12 medium supplemented with 10% FBS, 100 U/ml penicillin, 0.1 mg/ml streptomycin, and 2.5 mg/ml amphotericin B, and this was replaced every 72 h. Human ASM cells in subculture during passages 1-5 were used, as these cells retain native contractile protein expression as demonstrated by immunocytochemical staining for smooth muscle actin and myosin (Panettieri et al. 1989).

Figure 2A:
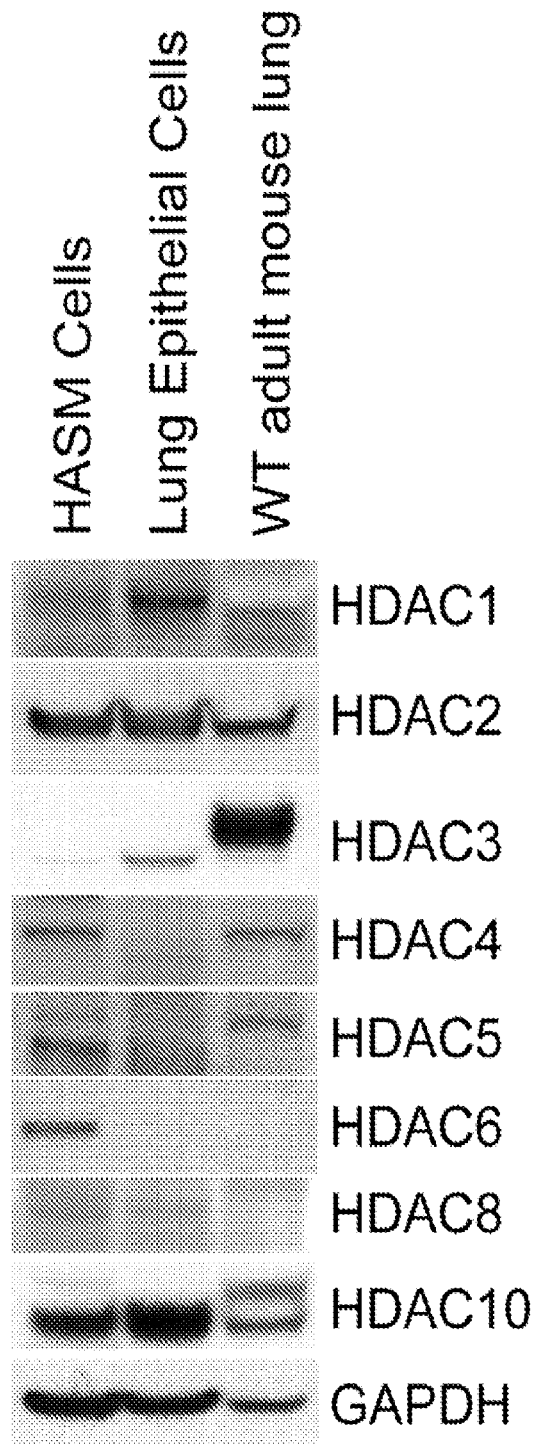
FIG. 2B. Relative HDAC activity from lung tissue lysate. Mice were sensitized (i.p.) and challenged (i.n.) with AF extracts or solvent (naïve) and those that received vehicle treatment (DMSO), or TSA 0.6 mg/kg i.p. Data are average results+/− S.D. from 5 samples for each condition.
Figure 2B:
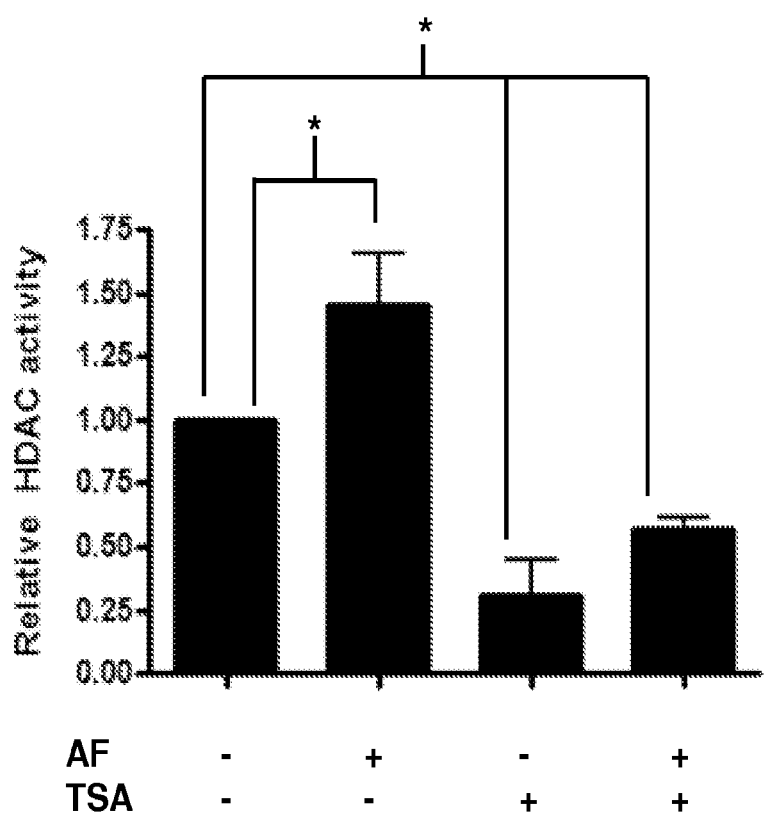

Example 1: HDAC is Expressed in Murine and Human Lung and TSA Inhibits HDAC Activity in Mice We examined the expression of class I and II HDACs in human and murine lung tissue by Western blotting and documented expression of multiple HDACs in this tissue (FIG. 2A). Interestingly, we observed that HDACs are expressed at different levels in human airway smooth muscle cells, human airway epithelial cells, and mouse lung. We subsequently examined the effects of a broad spectrum class 1 and 2 HDAC inhibitor, TSA, on lung physiology. First, we measured HDAC activity in lung tissue from naïve mice and mice treated with TSA. While mice had some HDAC activity at baseline, which was significantly increased with *Aspergillus* sensitization and challenge, TSA at the dose used in this study effectively inhibited HDAC activity in naïve mice and in mice sensitized and challenged with *Aspergillus* to induce an allergic response (FIG. 2B).

Figure 3A:
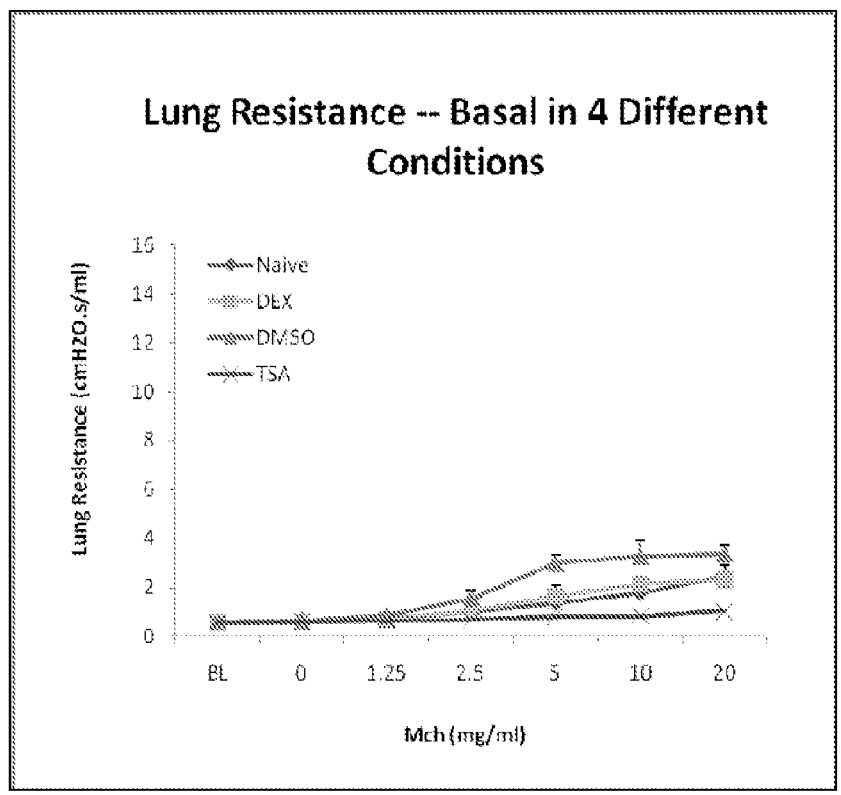
FIG. 3. Lung resistance of naïve and vehicle-treated (DMSO), HDAC inhibitor-treated (TSA 0.6 mg/kg i.p.) or dexamethasone-treated (2.5 mg/kg i.p.) ventilated mice (basal condition), in response to increasing doses of methacholine measured by the Scireq FlexiVent system (FIG. 3A).
In FIG. 3B, the Y-axis range was altered from FIG. 3A to show the differences among the cohorts in basal conditions.
Figure 3B:
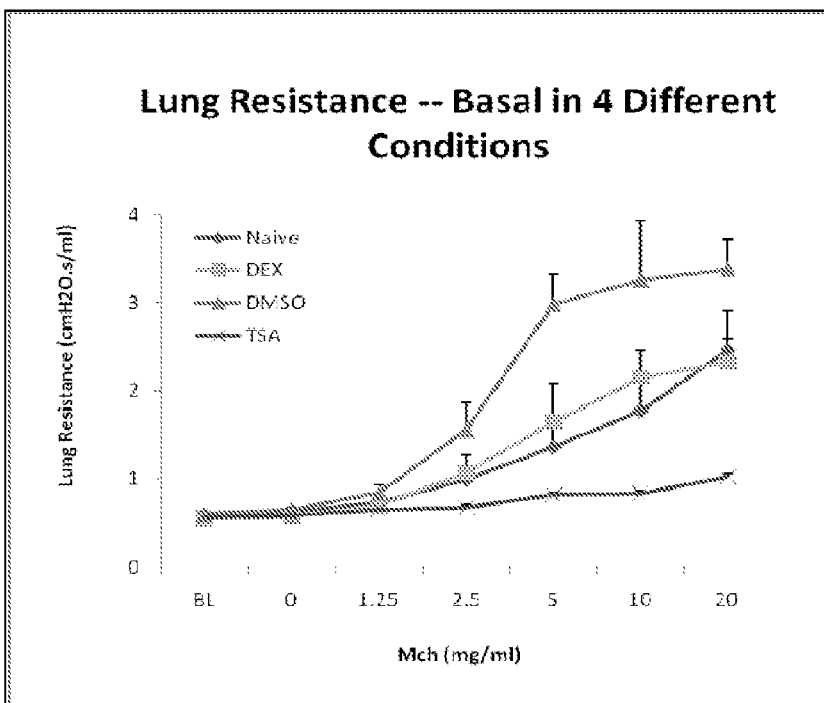

Example 2: HDAC Inhibition Decreases Carbachol Induced Increases in Resistance and Compliance Next, we examined the effects of TSA administration on lung resistance and compliance in mice challenged with increasing doses of methacholine. As shown in FIG. 3A-B, intraperitoneal DMSO (which we used as a control and to dissolve and deliver TSA) increased airway resistance in response to methacholine compared to untreated mice (Emax 3.5 cmH2O/mL) and intraperitoneal administration of TSA (0.6 mg/kg) suspended in DMSO attenuated this response (Emax 1.0 cmH2O/mL). Treatment with dexamethasone decreased airway resistance in response to methacholine, but to a lesser extent than TSA (Emax 2.3 cmH2O/mL). Interestingly, TSA treatment diminished lung resistance to methacholine challenge to below baseline (Emax 2.3 cmH2O/mL). Thus, TSA inhibited basal responsiveness to the bronchoconstrictor methacholine.

Figure 4:
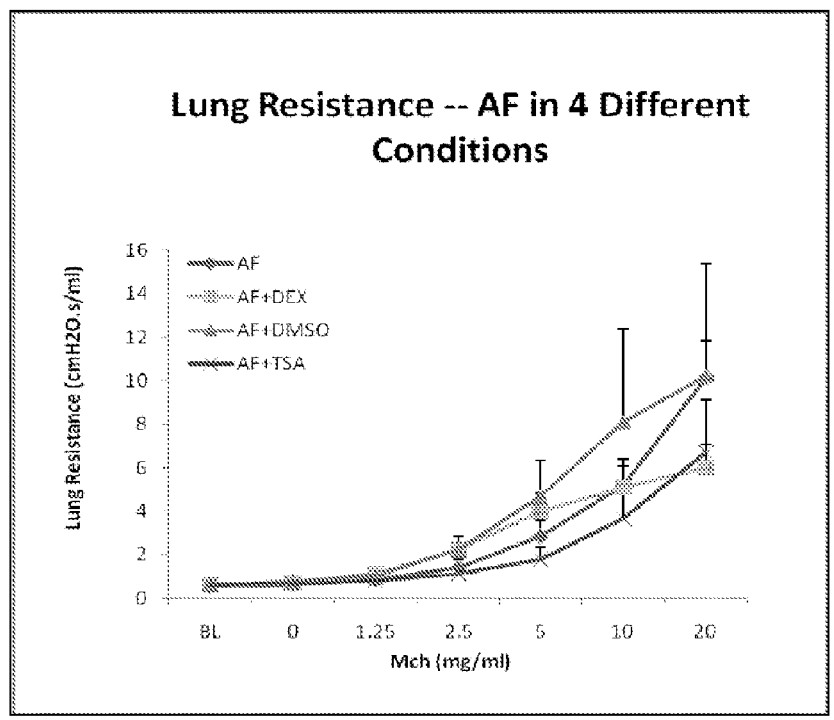
FIG. 4. Lung resistance from mice that were sensitized (i.p.) and challenged (i.n.) with *Aspergillus fumigatus* (AF) extracts and received vehicle treatment (DMSO), HDAC inhibitor treatment (TSA 0.6 mg/kg i.p.) or dexamethasone (2.5 mg/kg i.p.). Methacholine responsiveness was measured by the Scireq FlexiVent system.

In mice sensitized to *Aspergillus*, resistance in both naïve and DMSO treated mice increased in response to methacholine when compared to naïve mice 9 (Emax 10.8 cmH2O/mL,) but treatment with TSA significantly blunted this response to methacholine challenge (Emax 6 cmH2O/mL) (FIG. 4). Dexamethasone inhibited airway resistance in response to methacholine challenge to a similar degree (Emax 6 cmH2O/mL). The half maximal effective concentration of methacholine was lowest in mice treated with DMSO (5 mg/mL), higher in naïve mice (10 mg/mL) and highest in mice treated with TSA or dexamethasone (20 mg/mL). Thus, TSA was as effective as dexamethasone in abrogating methacholine-induced airway hyperresponsiveness.

Figure 5:
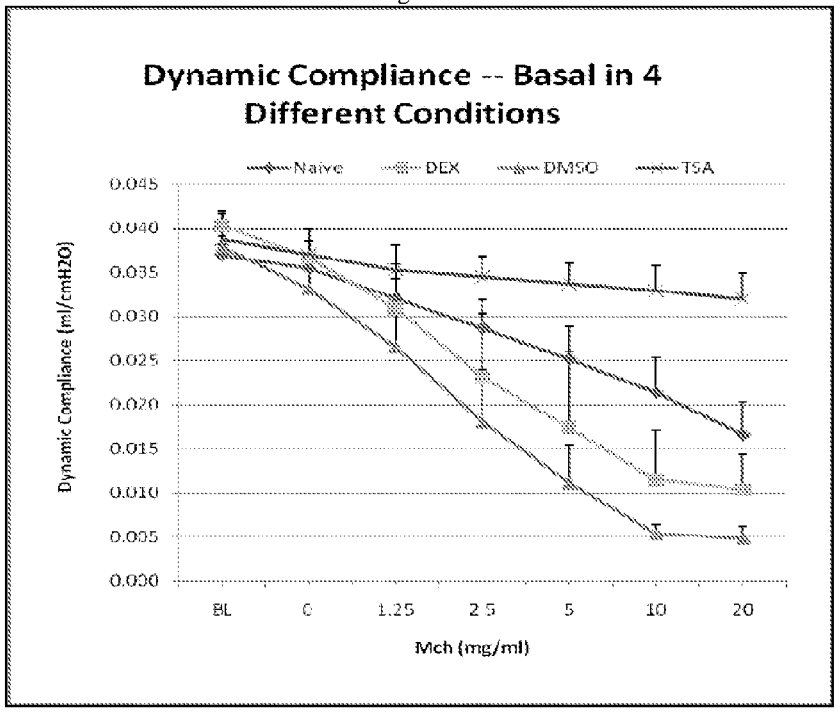
FIG. 5. Dynamic compliance from naïve mice and those treated with vehicle (DMSO), TSA 0.6 mg/kg i.p. or dexamethasone (2.5 mg/kg i.p.), in response to increasing doses of methacholine measured by the Scireq FlexiVent system.

When we tested dynamic compliance in response to methacholine challenge (FIG. 5), we observed that mice challenged with methacholine show a reduction in dynamic compliance, with a maximum inhibition to 0.017 ml/cmH2O. While DMSO treatment further decreases dynamic compliance in response to methacholine to a maximum inhibition of 0.005 ml/cmH2O, treatment with TSA inhibits the reduction in dynamic compliance after methacholine challenge and the maximum inhibition is 0.032 mL/cmH2O. The maximum inhibition of compliance by methacholine in dexamethasone treated mice was 0.010 mL/cmH2O. The half maximal inhibitory concentration of methacholine on dynamic compliance was 2.5 mg/mL in naive mice, 1.25 mg/mL in mice treated with DMSO, and 2 mg/mL in dexamethasone treated mice, and 2.5 mg/mL in TSA treated mice. Thus, TSA markedly inhibits methacholine-induced decreases in dynamic compliance.

Figure 6:
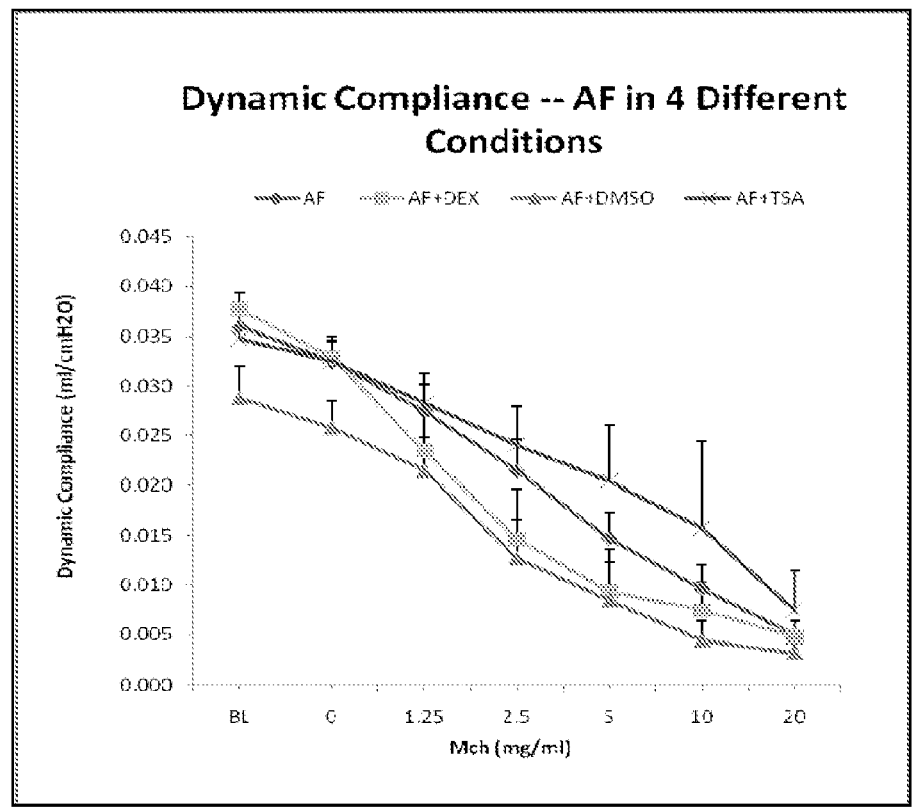
FIG. 6. Dynamic compliance from mice that are sensitized (i.p.) and challenged (i.n.) with AF or solvent (naïve) and those that received vehicle treatment (DMSO), TSA 0.6 mg/kg i.p. or dexamethasone (2.5 mg/kg i.p.). Methacholine-induced decreases in dynamic compliance were measured by the Scireq FlexiVent system.

In mice sensitized to *Aspergillus* and challenged with methacholine (FIG. 6), untreated mice, DMSO treated mice, dexamethasone treated mice all had a maximum inhibition of 0.005 mL/cmH2O, and mice treated with TSA had a maximum inhibition of 0.008 mL/cmH2O. In these mice, the half maximal inhibitory concentration of methacholine on dynamic compliance was 2.5 mg/mL in untreated mice, 1.25 mg/mL in mice treated with DMSO, 1.5 mg/mL in dexamethasone treated mice, and 5 mg/mL in TSA treated mice.

Together, these data demonstrate that treatment with TSA diminished lung resistance and increased dynamic compliance in methacholine challenged mice at baseline and in the setting of *Aspergillus* sensitization. Further, TSA reduced airway hyperresponsiveness more effectively than dexamethasone.

Figure 7:
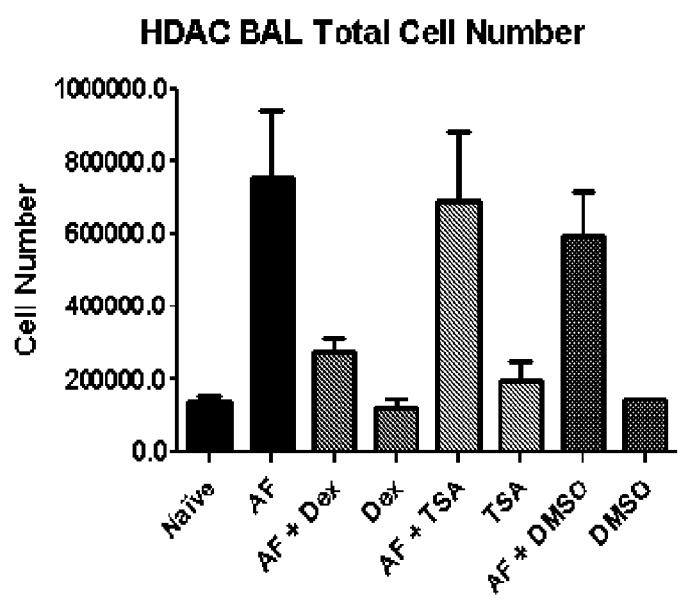
FIG. 7. The total number of cells obtained from bronchoalveolar lavage (BAL) fluid from mice that were sensitized (i.p.) and challenged (i.n.) with AF extracts or solvent (naïve) and those that received vehicle treatment (DMSO), TSA 0.6 mg/kg i.p. or dexamethasone (2.5 mg/kg i.p.).

Example 3: Effects of TSA on Cell Counts and Differential in Bronchoalveolar Lavage We next examined the bronchoalveolar lavage (BAL) fluid of naïve mice and those sensitized to *Aspergillus* and treated with dexamethasone and/or TSA (FIG. 7). Naive mice treated with dexamethasone, TSA, or DMSO showed no significant difference in cell counts. As expected, treatment with *Aspergillus* increased cell counts in BAL when compared to naïve mice. Dexamethasone decreased the total cell counts in BAL of *Aspergillus* sensitized and challenged mice, while TSA and DMSO had no effect. Thus, TSA had little effect on inflammatory cell trafficking into the BAL.

Figure 8:
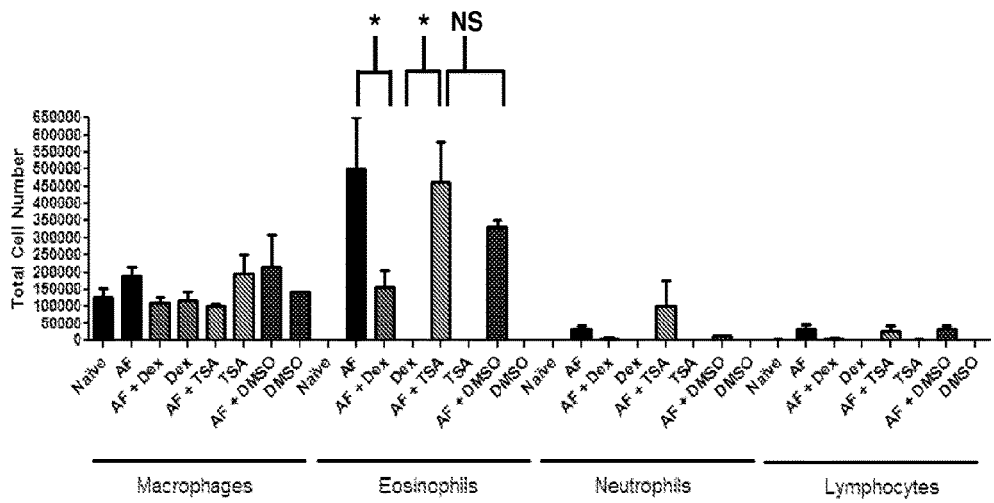
FIG. 8. The cellular profile of BAL from mice that were sensitized (i.p.) and challenged (i.n.) with AF extracts or solvent (naïve) and those that received vehicle treatment (DMSO), TSA 0.6 mg/kg i.p. or dexamethasone (2.5 mg/kg i.p.).

Mice challenged with *Aspergillus* had increased eosinophil counts (FIG. 8). While treatment with dexamethasone decreased BAL eosinophils, TSA and DMSO had no effect. There were no significant differences in macrophages, neutrophils, or lymphocytes in untreated mice or mice sensitized and challenged with *Aspergillus* treated with TSA, dexamethasone, or DMSO. Thus, TSA had little effect on cell trafficking into the lung after allergen sensitization and challenge.

Figure 9:
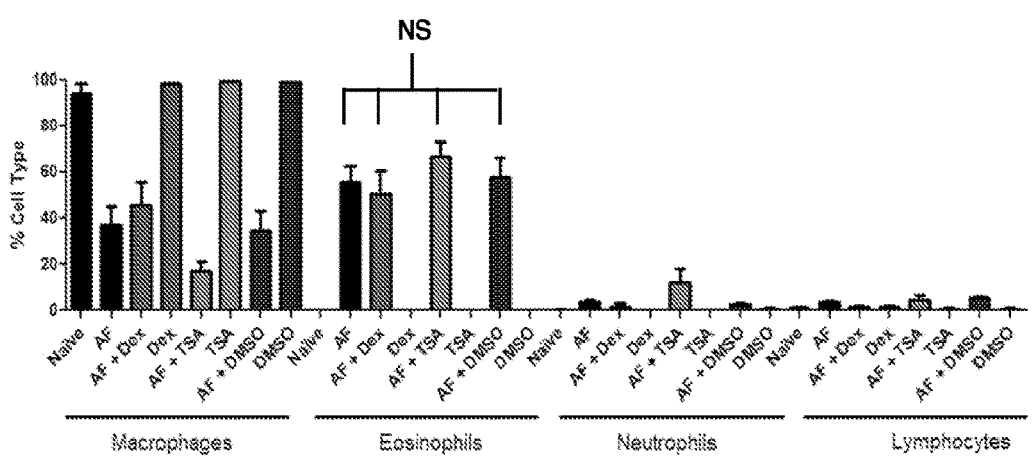
FIG. 9. The cellular profile of BAL from mice that were sensitized (i.p.) and challenged (i.n.) with AF extracts or solvent (naïve) and those that received vehicle treatment (DMSO), TSA 0.6 mg/kg i.p. or dexamethasone (2.5 mg/kg i.p.).

When we evaluated the percent cell types in the BAL of mice treated with dexamethasone and/or TSA that were naïve or sensitized and challenged with *Aspergillus*, we found that BAL of naïve mice contained mainly macrophages, and sensitization and challenge with *Aspergillus* decreased the macrophage percent while increasing the percent of eosinophils (FIG. 9). Thus, treatment with TSA or dexamethasone had little effect on percentages of inflammatory cells in the BAL after allergen sensitization and challenge.

These data demonstrate that while both dexamethasone and TSA inhibit airway hyperresponsiveness in response to methacholine, dexamethasone inhibits inflammatory cell migration into the BAL, while TSA does not.

Figure 10A:
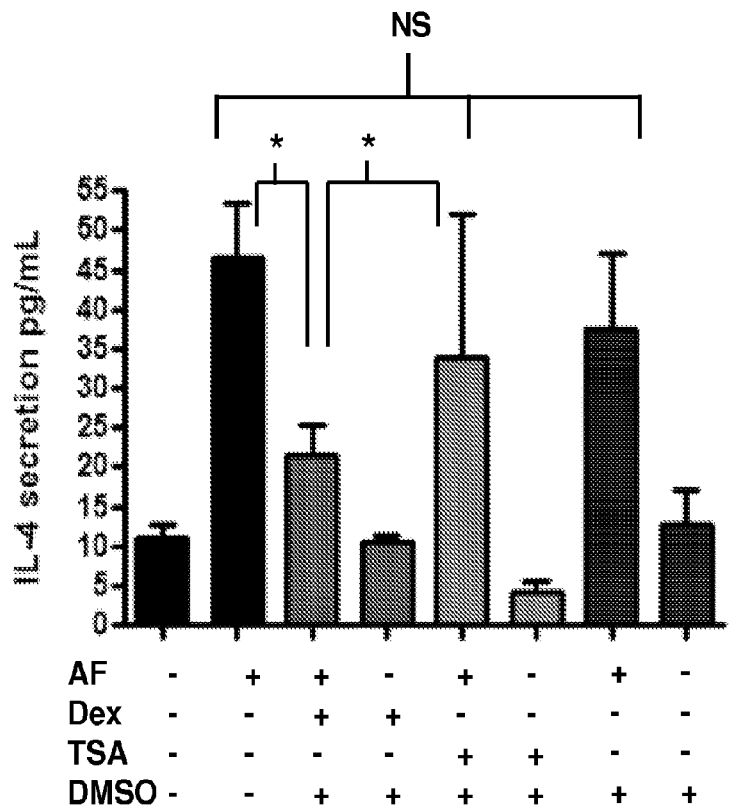
FIG. 10. IL-4 (FIG. 10a) and IL-6 (FIG. 10b) levels from BAL from mice that were sensitized (i.p.) and challenged (i.n.) with AF extracts or solvent (naïve) and those that received vehicle treatment (DMSO), TSA 0.6 mg/kg i.p. or dexamethasone (2.5 mg/kg i.p.).
Figure 10B:
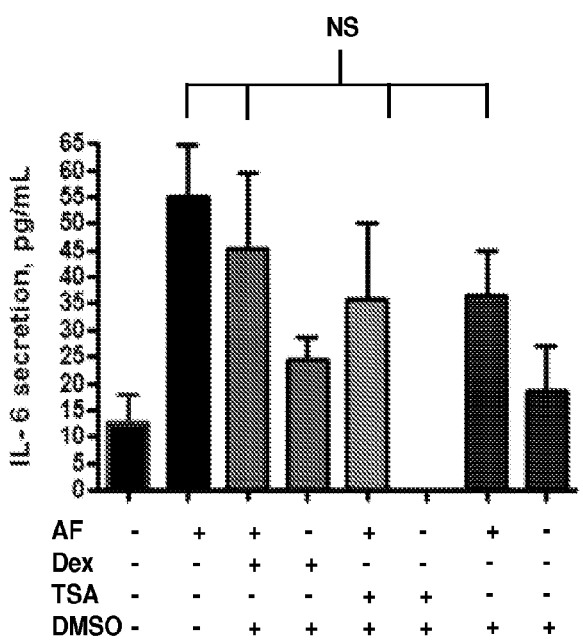

Example 4: Effect of TSA on Levels of Inflammatory Chemokines in the BAL of Naïve and *Aspergillus* Sensitized and Challenged Mice IL-4 and IL-6 are inflammatory cytokines implicated in asthma. In naïve mice, there were negligible levels of both IL-4 and IL-6 in the BAL (FIGS. 10A-B) and treatment with dexamethasone, DMSO, or TSA did not increase IL-4 or IL-6 in BAL of unsensitized and unchallenged mice. Mice sensitized and challenged with *Aspergillus* had elevations of both IL-4 and IL-6 in the BAL, and dexamethasone attenuated these elevations. Treatment with DMSO or TSA, on the other hand, had little effect on cytokine secretion in mice sensitized and challenged with allergen. These data show that while TSA treatment abrogates bronchoconstriction in response to allergic sensitization and challenge, it does not affect inflammatory chemokine secretion in the BAL.

Figure 11A:
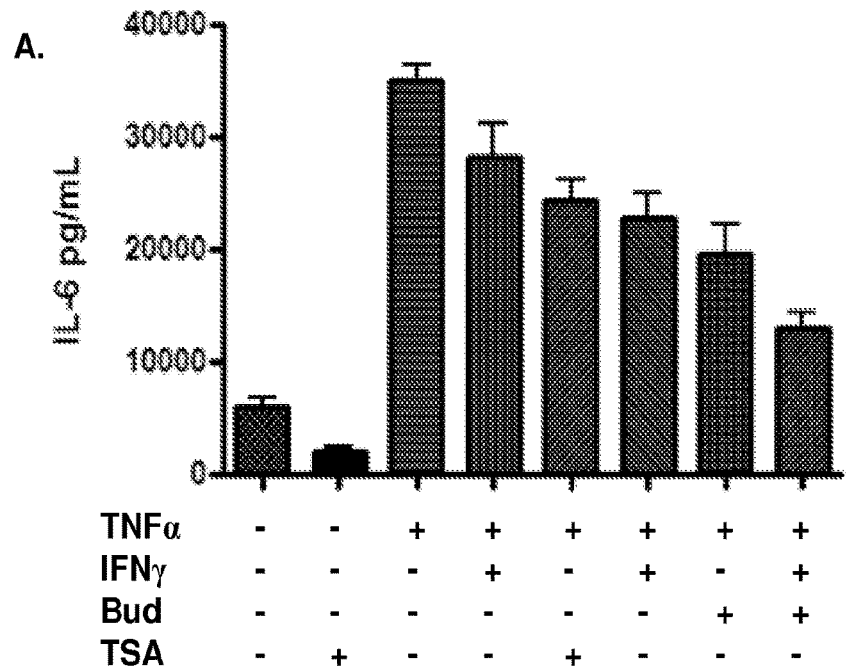
FIG. 11. IL-6 (FIG. 11A) and RANTES (FIG. 11b) secretion from precision cut lung slices (PCLS) treated with TSA (10 µM) or Budesonide (50 nM) 2 h prior to stimulation with TNFα (10 ng/mL) or a combination of TNFα (10 ng/mL) and IFNγ (10,000 IU/mL). Secretion of IL-6 and RANTES was analyzed as described under materials and methods. Values shown are mean+/− s.d. from three samples.

Example 5: TSA Treatment Decreases Chemokine Secretion From Precision Cut Lung Slices To test the effects of HDAC inhibition on chemokine secretion in human tissue, we treated precision cut lung slices (PCLS) with TSA or the glucocorticoid steroid budesonide, then exposed the cells to tumor necrosis factor alpha (TNFα), an inflammatory cytokine implicated in asthma, or a combination of TNFα and interferon gamma (IFNγ), a cytokine implicated in viral infections. Our prior work has demonstrated that both cytokines can induce chemokine synthesis alone and in combination, and the combination of TNFα and IFNγ induces steroid insensitive chemokine secretion (Banerjee et al 2008). Additionally, TNFα stimulation induces HAT activity in ASM, and stimulation with a combination of TNFα and IFNγ diminishes HAT activity induced by TNFα and greatly increases HDAC activity (Keslacy et al 2007). After stimulation with cytokines, we analyzed the supernatant for IL-6 and RANTES secretion as described in the methods. As shown in FIG. 11A, untreated cells had little IL-6 secretion, and TSA treatment had little effect on basal IL-6 secretion. Stimulation with TNFα increased IL-6 secretion to $3.4 \times 10^4$ pg/ml, and treatment with budesonide inhibited IL-6 secretion by 44.4%+/−12.7%, (p=0.01). TSA treatment also decreased IL-6 secretion from PCLS by 30.2%+/−12.5% (p=0.03). IL-6 levels in PCLS stimulated with a combination of TNFα and IFNγ were lower than they were in PCLS stimulated with TNFα alone, although they were increased from basal levels. TSA treatment inhibited IL-6 secretion from PCLS stimulated with a combination of TNFα and IFNγ 18.8%+/−6.8%, and budesonide treatment decreased IL-6 secretion from PCLS stimulated with a combination of TNFα and IFNγ 52.7%+/−10.6%.

Figure 11B:
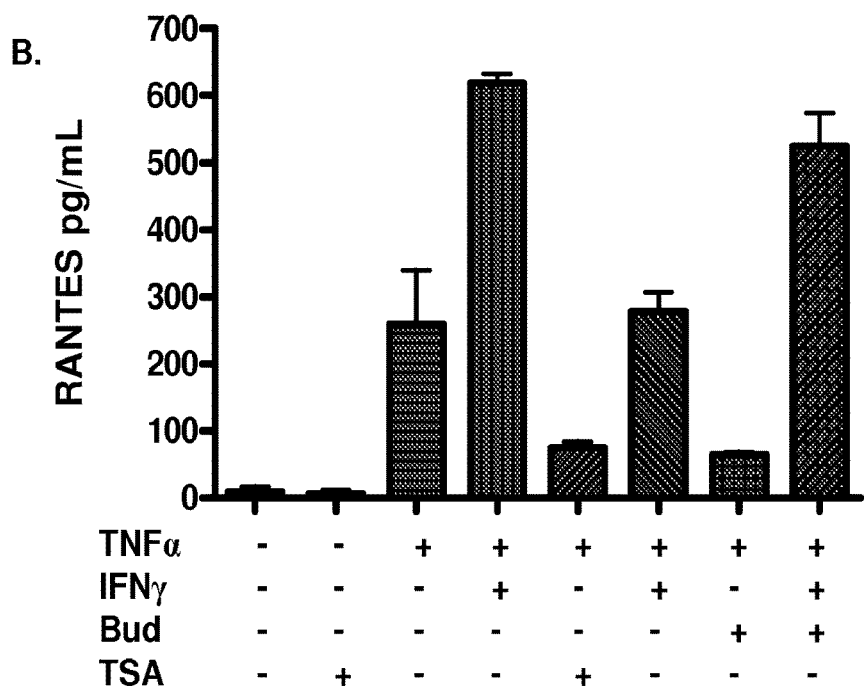

Similarly, TSA treatment did not induce basal RANTES secretion but inhibited TNFα induced RANTES secretion by 50%+/−23% (p=0.04). Budesonide treatment decreased TNFα induced RANTES secretion 69%+/−13% (p<0.01) (FIG. 11B). Stimulation of PCLS with a combination of TNFα and IFNγ increased RANTES secretion compared to stimulation with TNFα alone, and while treatment with budesonide did not significantly inhibit RANTES secretion from PCLS treated with TNFα and IFNγ, treatment with TSA inhibited TNFα and IFNγ induced RANTES secretion by 55.1%+/−7.5% (p<0.001). These data suggest that, unlike our findings in mouse BAL, treatment of PCLS with TSA can inhibit secretion of chemokines induced by inflammatory cytokine stimulation, and TSA treatment can inhibit steroid insensitive secretion of RANTES.

In summary, this study demonstrated that administration of TSA, an inhibitor of HDAC activity, abrogates methacholine induced increases in airways resistance in both naïve and allergen sensitized and challenged mice. Additionally, we demonstrated that TSA inhibits airway hyperresponsiveness in mouse lung without affecting leukocyte trafficking or chemokine secretion in the BAL. These effects are distinct from the effects of glucocorticoids such as dexamethasone, which, in our experiments, were able to decrease eosinophil trafficking and secretion of IL-6 into the BAL while inhibiting airway hyperresponsiveness. Together these data suggest that HDAC inhibition works by a mechanism distinct from glucocorticoids, and suggests an exciting new therapeutic pathway for asthmatics. The results as provided herein show that treatment with TSA was even more beneficial than treatment with dexamethasone. This treatment appeared to act directly on pulmonary smooth muscle cells and did not affect inflammation in the lung. Moreover, this treatment may be additive with dexamethasone.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for dilating the bronchi or bronchioles in a subject in need thereof, comprising the step of administering to said subject a composition comprising an effective amount of a histone deacetylase (HDAC) inhibitor, wherein administering said effective amount of said composition does not affect the number of eosinophils or IL-4 levels in bronchoalveolar lavage (BAL) fluid.

2. The method of claim 1, wherein said dilating the bronchi or bronchioles is treating or preventing bronchoconstriction.

3. The method of claim 1, wherein said subject is afflicted with a disorder of the respiratory muscles.

4. The method of claim 1, wherein said HDAC inhibitor is a pulmonary smooth muscle relaxant.

5. The method of claim 1, wherein said HDAC inhibitor is a hyroxamic acid.

6. The method of claim 1, wherein said HDAC inhibitor is Trichostatin A (TSA).

7. The method of claim 1, wherein said HDAC inhibitor is Vorinostat (SAHA).

8. The method of claim 1, wherein said composition is an oral pharmaceutical composition and the step of administering comprises orally administering.

9. The method of claim 8, wherein said oral pharmaceutical composition is a pill, a capsule, a tablet, a granule, a suspension, a solution, or a powder.

10. The method of claim 1, wherein said composition further comprises a steroid, a beta2 agonist, ipatropium bromide, theophylline, or any combination thereof.

11. The method of claim 10, wherein said steroid is dexamethasone.

12. The method of claim 1, wherein said subject is insensitive to steroid treatment.

* * * * *